US009588035B2

(12) United States Patent
Sun et al.

(10) Patent No.: US 9,588,035 B2
(45) Date of Patent: Mar. 7, 2017

(54) SYSTEM AND METHOD FOR FETAL AND MATERNAL RED BLOOD CELL COUNTING

(71) Applicant: The Governing Council Of The University Of Toronto, Toronto (CA)

(72) Inventors: Yu Sun, Toronto (CA); Ji Ge, Toronto (CA); Zheng Gong, Toronto (CA); Chen Wang, Toronto (CA); John Nguyen, Toronto (CA); Jun Liu, Toronto (CA); Jun Chen, Toronto (CA)

(*) Notice: Subject to any disclaimer, the term of this patent is extended or adjusted under 35 U.S.C. 154(b) by 0 days.

(21) Appl. No.: 14/422,291

(22) PCT Filed: Sep. 6, 2013

(86) PCT No.: PCT/CA2013/050685
§ 371 (c)(1),
(2) Date: Feb. 18, 2015

(87) PCT Pub. No.: WO2014/040184
PCT Pub. Date: Mar. 20, 2014

(65) Prior Publication Data
US 2015/0204771 A1    Jul. 23, 2015

Related U.S. Application Data

(60) Provisional application No. 61/700,659, filed on Sep. 13, 2012.

(51) Int. Cl.
*G06K 9/00* (2006.01)
*G01N 15/10* (2006.01)
(Continued)

(52) U.S. Cl.
CPC ......... *G01N 15/10* (2013.01); *G01N 15/1463* (2013.01); *G01N 33/49* (2013.01);
(Continued)

(58) Field of Classification Search
CPC ......... G06T 7/0012; G06T 2207/10024; G06T 2207/10056; G06T 2207/30024;
(Continued)

(56) References Cited

U.S. PATENT DOCUMENTS 5,764,792 A * 6/1998 Kennealy ........... G06K 9/00127
250/462.1

FOREIGN PATENT DOCUMENTS

CA  PCT/CA2013/050685    *  4/2014
EP         1373854 A2  *  1/2004
WO        02079749 A2    10/2002

OTHER PUBLICATIONS

"Improved of the Kleinhauer-Betke test by Automated Detection of Fetal Erythrocytes in Maternal Blood" Pelikan et al. Cytometry Part B, Clinical cytometry, vol. 54, No. 1, pp. 1 to 19, Jul. 19, 2003.*
(Continued)

*Primary Examiner* — Gregory F Cunningham
(74) *Attorney, Agent, or Firm* — Eduardo Krupnik

(57) ABSTRACT

A system for counting fetal and maternal red blood cells (RBCs) including a microscope and image capturing device to capture at least one image from a slide holding the fetal and maternal RBCs; a computer readable medium for storing the at least one image; a processor for executing computer readable instructions stored on a computer readable medium; wherein the computer executable instructions include instructions for: indentifying red blood cells from the at least one image; distinguishing between fetal and maternal red blood cells; and counting the fetal and maternal red blood cells.

27 Claims, 13 Drawing Sheets

(51) Int. Cl.
  *G01N 33/49* (2006.01)
  *G02B 21/26* (2006.01)
  *G06T 7/00* (2006.01)
  *G01N 15/00* (2006.01)
  *G01N 15/14* (2006.01)

(52) U.S. Cl.
  CPC ......... *G02B 21/26* (2013.01); *G06K 9/00134* (2013.01); *G06T 7/0012* (2013.01); *G01N 2015/0073* (2013.01); *G01N 2015/1062* (2013.01); *G01N 2015/1465* (2013.01); *G06T 2207/10024* (2013.01); *G06T 2207/10056* (2013.01); *G06T 2207/30024* (2013.01); *G06T 2207/30242* (2013.01)

(58) Field of Classification Search
  CPC ...... G06T 2207/30242; G06K 9/00134; G02B 21/26; G01N 15/10; G01N 2015/0073; G01N 2015/1062; G01N 33/49
  USPC ........................................................ 382/134
  See application file for complete search history.

(56) References Cited

OTHER PUBLICATIONS

International preliminary report, (PCT/CA2013/050685), Apr. 2014, Canada, Carole Millaire.*

"Automated Red Blood Cell Counting" Hamouda et al, International Journal of Computing Science, vol. 1, No. 2, Feb. 2012, ISSN (Print): 2164-1366, ISSN (Online): 2164-1374.

"Automatic red blood cell counting using Hough transform" Venkatalakshmi et al, Information & Communication Technologies (ICT), 2013 IEEE Conference, pp. 267-271, Apr. 12, 2013.

Image-based red cell counting for wild animals blood, Mauricio et al. Engineering in Medicine and Biology Society (EMBC), 2010 Annual International Conference of the IEEE, Sep. 4, 2010.

"Improved red blood cell counting in thin blood smears",Berge et al, Biomedical Imaging: From Nano to Macro, 2011 IEEE International Symposium Apr. 2, 2011.

"Comparison of Red Blood Cells Counting Using Two Algorithms: Connected Component Labeling and Backprojection of Artificial Neural Network", Nasution et al, 2008.

"An Unparagoned Application for Red Blood Cell Counting using Marker Controlled Watershed Algorithm for Android Mobile", Next Generation Mobile Applications, Services and Technologies (NGMAST), Karunakar et al, 2011 5th International Conference on Sep. 2011.

"A novel method and count the red blood cells in thin blood films", Circuits and Systems (ISCAS), Kareem et al, 2011 IEEE International Symposium on May 18, 2011.

* cited by examiner

SYSTEM AND METHOD FOR FETAL AND MATERNAL RED BLOOD CELL COUNTING

This application claims priority from U.S. Provisional Application No. 61/700,659, filed Sep. 13, 2012 the contents of which, in their entirety, are herein incorporated by reference.

FIELD OF THE INVENTION

The present invention relates generally to the field image processing for cell analysis, and in particular to a system and method for differentiating between, and counting, fetal and maternal red blood cells

BACKGROUND OF THE INVENTION

In North America, there are over 6 million pregnancies annually. Rhesus hemolytic (Rh) disease of the newborn is a serious alloimmune condition, where fetal red blood cells (RBCs) are destroyed by the maternal immune system through the placenta. During pregnancy or child birth, a small number of fetus's RBCs can enter the mother's circulation. If the mother is Rh negative and the fetus is Rh positive, the mother's body produces antibodies (IgG) against the Rh antigen. This process is termed sensitizing. Most frequently, sensitizing occurs during child birth (about 85% of sensitized cases), but fetal blood may pass into the maternal circulation earlier during the pregnancy (about 15% of sensitized cases) (see J. M. Bowman and J. M. Pollock, "Rh-Immunization during Pregnancy and Grandmother Theory," Journal of Pediatrics, vol. 93, pp. 313-314, 1978). During this or subsequent pregnancies the IgG is able to pass through the placenta into the fetus and consequently cause the destruction of the Rh positive fetal RBCs.

In Caucasian populations about 1 in 10 of all pregnancies are of a Rh negative woman with a Rh positive baby, of which 13% Rh negative mothers are sensitized (see A. S. Prasad, Ed., Acquired hemolytic anemias. In: Bick R L, ed. Hematology: Clinical and Laboratory Practice. St. Louis: Mosby-Yearbook, Inc., 1993). Besides the resulting anemia, fetal-maternal hemorrhage may have devastating consequences for the fetus such as neurologic injury, stillbirth, or neonatal death (B. J. Wylie and M. E. D'Alton, "Fetomaternal hemorrhage" Obstet. Gynecol., Vol. 115, pp. 1039-51, 2010). Many babies who managed to survive would be severely ill. The diagnosis and treatment require quantifying fetal-maternal hemorrhage (i.e., the amount of fetal blood that has passed into the maternal circulation), which is usually performed on Rhesus-negative mothers to determine the required dose of the drug, Rho(D) immune globulin (RhIg) to inhibit the formation of Rh antibodies in the mother and prevent Rh disease in future Rh-positive children.

Besides Rh diseases, fetal-maternal hemorrhage can also result from the loss of integrity of the normal physiological barrier between the fetal and maternal circulation, which must be quantified in pregnancy care for prompt treatment (e.g., blood transfusion) (C. J. Chen, S. N. Cheng, C. M. Lee, F. W. Chang, C. C. Wu, and Y. S. Yuh, "Fetomaternal hemorrhage," J. Med. Sci., Vol. 23, pp. 231-34, 2003). The standard clinical method of quantifying fetal-maternal hemorrhage is the Kleihauer-Betke (KB) test (Z. Y. Wang, J. W. Shi, Y. L. Zhou, and C. G. Ruan, "Detection of red blood cell-bound immunoglobulin G by flow cytometry and its application in the diagnosis of autoimmune hemolytic anemia," International Journal of Hematology, vol. 73, pp. 188-193, 2001). The test takes advantage of the differential resistance of fetal and maternal hemoglobin to acid (fetal hemoglobin is significantly more resistant). A standard blood smear is prepared from the mother's blood (1:1,000 dilution with PBS). After drying, staining and incubating, the blood smear slides are counted under a microscope by certified technologists. Since the fetal hemoglobin is resistant to the citrate buffer, the resulting bright-pink cells are classified as fetal cells. The percentage of fetal-maternal hemorrhage can then be calculated.

The critical component of the KB test is the counting of fetal and maternal RBCs. This counting is presently done manually by trained technologists who look into the eyepieces of a microscope and count a minimum of 2,000 cells. Manual counting takes about 15 minutes and inherently suffers from inconsistency and unreliability.

Although the term 'automated detection of fetal RBCs' was mentioned in the literature, there have been no reported approaches for automated counting of fetal and maternal RBCs, and there have been no reported approaches for distinguishing these two types of cells. In the work reported in the literature (see D. M. V Pelikan, W. E. Mesker, S. a Scherjon, H. H. H. Kanhai, and H. J. Tanke, "Improvement of the Kleihauer-Betke test by automated detection of fetal erythrocytes in maternal blood," Cytometry. Part B, Clinical cytometry, vol. 54, no. 1, pp. 1-9, July 2003 and see D. M. Pelikan, S. a Scherjon, W. E. Mesker, G. M. de Groot-Swings, G. G. Brouwer-Mandema, H. J. Tanke, and H. H. Kanhai, "Quantification of fetomaternal hemorrhage: a comparative study of the manual and automated microscopic Kleihauer-Betke tests and flow cytometry in clinical samples," American journal of obstetrics and gynecology, vol. 191, no. 2, pp. 551-7, August 2004), automation in these works refers to the use of commercial motorized stage to capture cell images. Images were captured first with a green filter, and images were captured again in a second scan with a red filter. Hence, image capturing required the use of a microscope equipped with a green absorption filter and a red absorption filter. Fetal RBCs were distinguished from maternal RBCs based on intensity and distribution patterns of staining by a technologist. The total cell number on a KB slide was also manually estimated.

Image processing methods have been developed for counting other types of cells, but not for counting RBCs. In one study (see N. Bandekar, A. Wong, D. Clausi and M. Gorbet, "A novel approach to automated cell counting for studying human corneal epithelial cells," Intn'l Conf. IEEE EMBS, Boston, pp. 5997-6000, 2011), cell counting was done via non-maximum suppression and seeded region growth to segment the clustering corneal epithelial cells. Nevertheless, only grey-level and spatial information were applied in this algorithm making it difficult to detect ghost cells and segment those clustered cells. In another study, the Hough circle transform was used to automatically count cell colonies in a culturing flask (see J. M. Bewes et al., "Automated cell colony counting and analysis using the circular Hough image transform algorithm (CHiTA)," Phys. Med. Biol., Vol. 53, pp. 5991-6008, 2008). Intensity gradient and circular Hough transform were used to discriminate the colony edges and detect cells. It was useful for quantifying low concentrations of cell colonies while under-segmentations are inevitable on those severely overlapping cells. Furthermore, contaminants cannot be excluded from the counting result.

Prior art patents include U.S. Pat. No. 6,341,180, U.S. Pat. No. 7,327,901 and U.S. Pat. No. 7,835,077 assigned to CellVision; and patent publications US2011/0170760 to Nextslide Imaging, US2010/0189338 to Nexcelom Bioscience, and US2012/0314092 to Bio-Rad Laboratories, Inc. The following three are considered relevant to the present invention.

"Network Image Review in Clinical Hematology", US2011/0170760 by Nextslide Imaging, disclosed a method for setting up an internet-based database for cell digital image analysis. Users upload cell images via the internet, and the images are processed on a remote server. No cell counting methods are disclosed.

U.S. Pat. No. 7,835,077, by CellaVision AB, "Microscope system comprising arrangement for positioning of a platform", describes a flexture system to adjust a specimen's vertical position for keeping the specimen within focus.

"Cell Counting System and Methods", as disclosed in US2012/0314092 by Bio-Rad Laboratories, Inc., introduced a system for counting cell numbers using digital images of a sample. The sample holder holding a set of cells is inserted into the slot of the system and the motion mechanism can change the relative positions of the sample holder automatically. Not more than three images are captured during the rotation and translation of the sample holder. The majority of areas on the sample are omitted making counting accuracy undependable. Furthermore, this system is applicable only to the testing of samples having low cell concentrations.

Accordingly, the prior art is silent on automated and sufficiently qualitative method or system for counting and distinguishing between maternal and fetal red blood cells. It is an object of the invention described below to provide a method and/or system that addresses at least one of the aforementioned problems with the prior art.

SUMMARY OF THE INVENTION

The system of this invention relates to computer vision algorithms (i.e., sequences of image processing steps) to work seamlessly with hardware components to automatically count total RBC numbers and distinguish fetal RBCs from maternal RBCs and adult F RBCs, based on their color, intracellular textures, roundness measure and size differences on standard KB slides.

To this end, and according to one embodiment of the invention, there is provided a system for counting fetal and maternal red blood cells (RBCs) including a microscope and image capturing device to capture at least one image from a slide holding the fetal and maternal RBCs; a computer readable medium for storing the at least one image; a processor for executing computer readable instructions stored on a computer readable medium. The computer executable instructions include instructions for identifying red blood cells from the at least one image, distinguishing between fetal and maternal red blood cells, and counting at least the fetal red blood cells; and preferably the maternal and total blood cells as well.

According to one aspect of this embodiment, the microscope is an X-Y stage microscope including an X-axis linear motion system and a Y-axis linear motion system.

According to another aspect of this embodiment, the microscope is in communication with a controller including a driver for each of the X and Y axis linear motion systems.

According to another aspect of this embodiment, the X-axis linear motion system and the Y-axis linear motion system are independently controllable.

According to another aspect of this embodiment, the at least one image comprises a plurality of images taken from different areas on the slide.

According to another aspect of this embodiment, the plurality of images comprises approximately 120 images.

According to another aspect of this embodiment, the image capturing device comprises a color camera controlled by the processor.

According to another aspect of this embodiment, the computer executable instructions for identifying red blood cells include instructions for converting the images into hue-saturation-value (HSV) color space and creating an N×3 matrix storing the H, S and V values for each pixel of the images.

According to another aspect of this embodiment, the computer executable instructions further include instructions for generating a first model (Model 1) and a second model (Model 2); wherein Model 1 is used to distinguish red blood cells from the image background and Model 2 is used to separate fetal red blood cells from maternal red blood cells.

According to another aspect of this embodiment, Model 1 is generated by computer executable instructions for detecting contours on each the images, and, circle fitting the contours using predetermined criteria for defining possible cells.

According to another aspect of this embodiment, the instructions further include an algorithm for identifying overlapping cells.

According to another aspect of this embodiment, the algorithm is a circular Hough transform algorithm.

According to another aspect of this embodiment, Model 2 is generated by computer executable instructions for converting each image to a gray image; and distinguishing potential fetal red blood cells from maternal red blood cells.

According to another aspect of this embodiment, the computer executable instructions further include instructions for generating a second gray image containing the potential fetal red blood cells and distinguishing between fetal red blood cells and adult F blood cells.

According to another aspect of this embodiment, the distinguishing of potential fetal red blood cells from maternal red blood cells includes an algorithm including feature vectors including at least one feature from the group consisting of cell size, roundness, gradient, saturation difference and a combination of same; and further wherein feature values for each of fetal red blood cells and maternal red blood cells are stored on the computer readable medium.

According to another aspect of this embodiment, the distinguishing of fetal red blood cells from adult F red blood cells includes an algorithm including feature vectors including at least one feature from the group consisting of cell size, roundness, gradient, saturation difference and a combination of same; and further wherein feature values for each of fetal red blood cells and adult F red blood cells are stored on the computer readable medium.

According to another aspect of this embodiment, the distinguishing is carried out using a supervised learning model selected from the group consisting of K-nearest neighbors, Gaussian mixtures, decision trees and other.

According to another aspect of this embodiment, the algorithms are unsupervised, self-learning algorithms.

According to a second embodiment of the invention, the system and method as herein described are used for conducting Kleihauer-Betke (KB) testing.

According to a third embodiment of the invention, there is provided a computer executable method for counting fetal and maternal red blood cells (RBCs) including obtaining by a camera mounted on a microscope at least one image from a slide, identifying by a computer processor red blood cells from the at least one image, distinguishing by the computer processor between fetal and maternal red blood cells and counting by the computer processor at least the fetal red blood cells.

According to one aspect of this embodiment, the at least one image comprises a plurality of images taken from different areas on the slide.

According to another aspect of this embodiment, the plurality of images comprises approximately 120 images.

According to another aspect of this embodiment, the method further includes converting the images into hue-saturation-value (HSV) color space and creating an N×3 matrix storing the H, S and V values for each pixel of the images.

According to another aspect of this embodiment, the method further includes generating a first model (Model 1) and a second model (Model 2); wherein Model 1 is used to distinguish red blood cells from the image background and Model 2 is used to separate fetal red blood cells from maternal red blood cells.

According to another aspect of the invention, Model 1 is generated by detecting contours on each the images and, circle fitting the contours using predetermined criteria for defining possible cells.

According to another aspect of the invention, Model 2 is generated by converting each image to a gray image, and distinguishing potential fetal red blood cells from maternal red blood cells.

According to another aspect of the invention, the method further includes generating a second gray image containing the potential fetal red blood cells and distinguishing between fetal red blood cells and adult F blood cells.

According to another aspect of the invention, the distinguishing of potential fetal red blood cells from maternal red blood cells includes executing an algorithm including feature vectors including at least one feature from the group consisting of cell size, roundness, gradient, saturation difference and a combination of same; and further wherein feature values for each of fetal red blood cells and maternal red blood cells are stored on a computer readable medium.

According to another aspect of the invention, the distinguishing of fetal red blood cells from adult F red blood cells includes executing an algorithm including feature vectors including at least one feature from the group consisting of cell size, roundness, gradient, saturation difference and a combination of same; and further wherein feature values for each of fetal red blood cells and adult F red blood cells are stored on the computer readable medium.

According to another aspect of the invention, the distinguishing is carried out using a supervised learning model selected from the group consisting of K-nearest neighbors, Gaussian mixtures, decision trees and other.

BRIEF DESCRIPTION OF THE DRAWINGS

Embodiments will now be described, by way of example only, with reference to the attached Figures, wherein.

DETAILED DESCRIPTION

Various embodiments of the invention relate to a mechanical system that includes an two-axis microscope moveable in the X-Y stage, which is preferably motorized to capture images which are subsequently processed in accordance with the below-described image processing methods to provide an automated, computer vision based approach to counting fetal and maternal red blood cells (hereinafter "RBCs").

A. Hardware System

Figure 1:
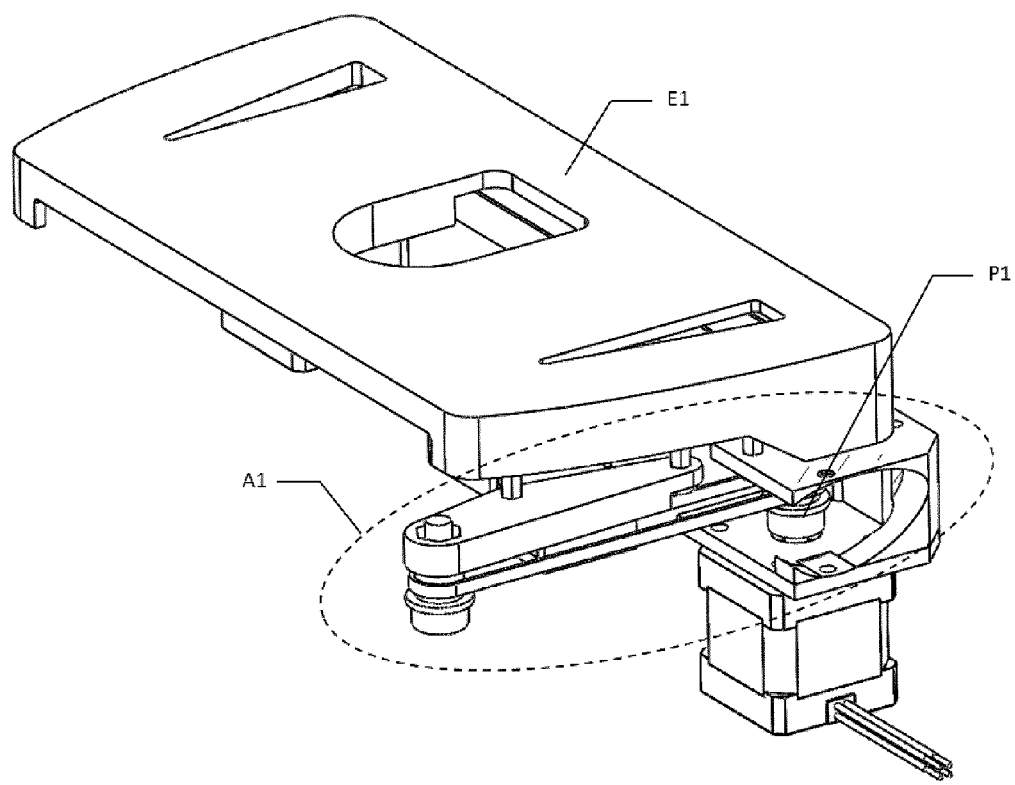
FIG. 1 is an isometric view of the X-axis of the motorized X-Y microscope stage.
Figure 2:
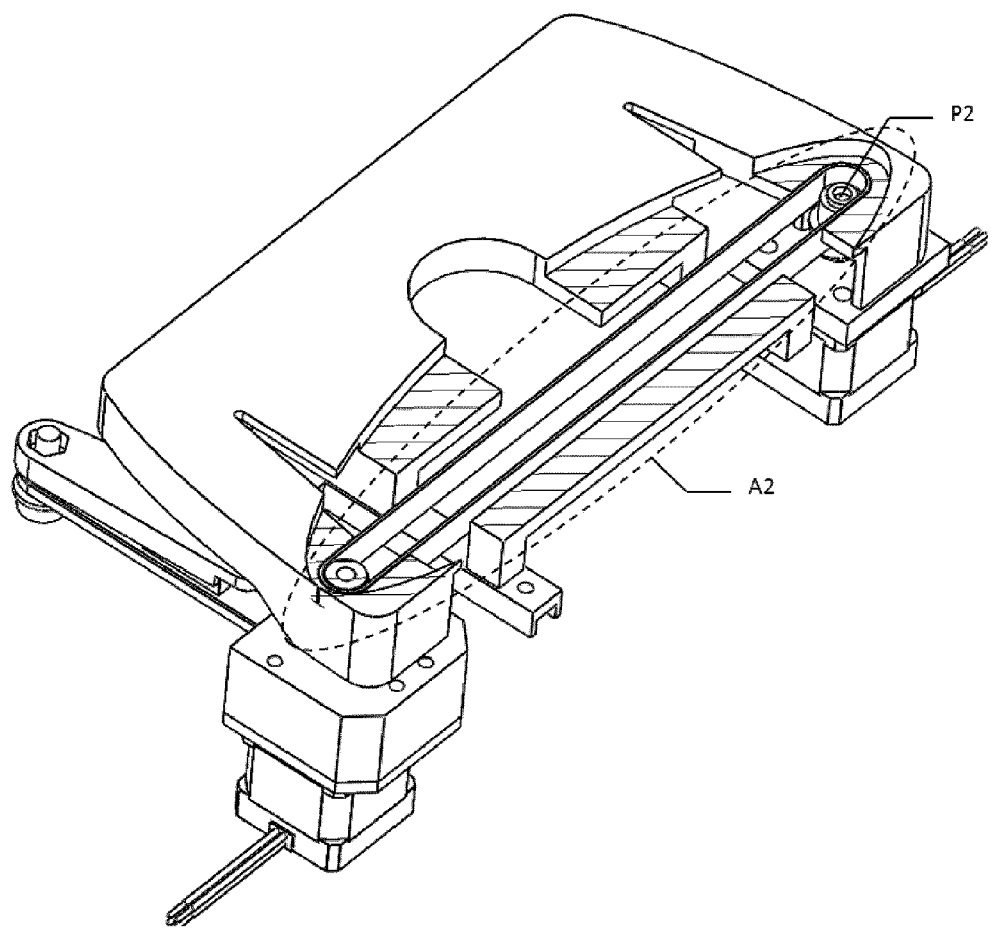
FIG. 2 is an isometric view of the Y-axis of the motorized X-Y microscope stage.

Referring now to FIGS. 1 and 2, there is shown an exemplary hardware system which may be used to capture images for processing in accordance with the invention. The system generally includes a modified manual X-Y stage microscope and components for motorizing and/or automating the movement of the microscope to capture the requisite images for processing as described further below. X-Y stage microscopes are generally known in the art and not described in further detail herein. As illustrated, the standard manual X-Y stage microscope 10 is moveable along linear bearings 20, and is equipped with two driving motor assemblies 30 and 40 which are preferably stepper motor assemblies having individual mounts and attachments to control movement of the microscope.

The standard X-Y stage microscope only allows manually driven linear motion. In order to provide the motorized motion, two stepper motor mounts are provided on each axis. Attachments to the manual X-Y stage consists of a combination of commercially available fasteners and custom components manufactured to be fitted onto the X-Y stage. Preferably, ABS is used for fabrication purposes of the mounts as it is less susceptible to plastic defects, such as warping. The stepper motor assemblies may use a driving system based on timing belts and pulleys. However, other types of rotational motion to linear motion systems are also contemplated by the invention.

Timing belt driven systems are ideal linear motion operations due to their low cost, compact implementation while maintaining a large range of possible gearing ratios. A properly tensioned timing belt driven system will lessen the effect of backlash inherent in toothed linear motion systems. It should be noted that a tensioning system could also be implemented using an active spring loaded mechanism or a passive tensioning mechanism as shown in FIG. 2. By modifying the diameter of the driving pulleys P1 and P2, the motion range and resolution of the assembly can be adjusted.

Figure 3:
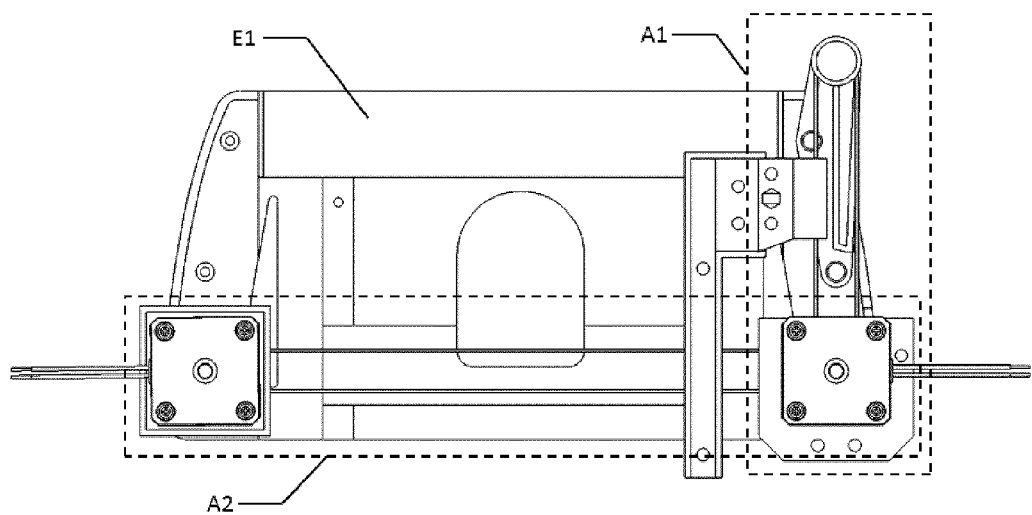
FIG. 3 is a bottom up view of the motorized modified X-Y microscope stage showing linear motion assembly and timing belt configuration.
Figure 4:
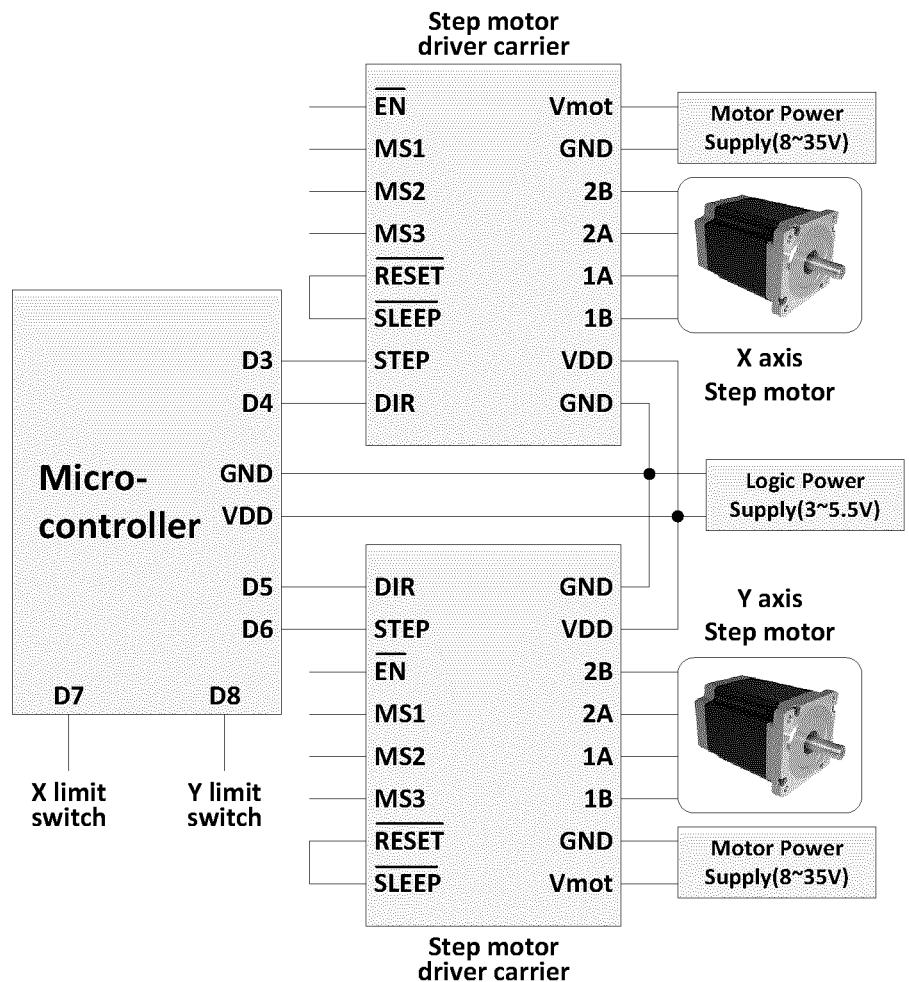
FIG. 4 shows an exemplary control method for controlling the motorized microscope of FIGS. 1-3.

As will become appreciated, accuracy in imaging windows is highly beneficial to the invention. To allow for positioning the exact imaging windows or complex movement sequences, axes need be independently controlled. FIG. 3 illustrates the orientation and positioning of both stepper motor assemblies, A1 and A2 to provide X and Y motion, respectively. The stepper motors may be controlled via stepper motor drivers which generate the appropriate signals to provide discrete steps, as illustrated in FIG. 4. The stepper motor driver is capable of accepting and processing G-code, a widely used and standardized language used in computer numerical control. Step sizes ranging from full, half, quarter, eighth and sixteenth steps are all available for adjustment via the stepper motor drivers to allow for various requirements in terms of speed, step resolution and torque output. The stepper motor drivers provide a signal such that a trapezoidal velocity profile is generated. All parameters including acceleration, desired speed and deceleration can be varied to suit the speed requirements as well as travel distance.

Real-time calculations of delay times between step pulses using an iterative approach is required to generate smoothened profiles. Care should be taken to monitor the immediate axis speed when accelerating and decelerating to ensure smooth and accurate plateau speeds. While a trapezoidal velocity profile still produces a discontinuous acceleration profile, a gradual change in acceleration upon approaching the plateau speed will allow for higher possible speeds with minimal jerk. This can improve motion accuracy and maximal speeds.

Figure 5:
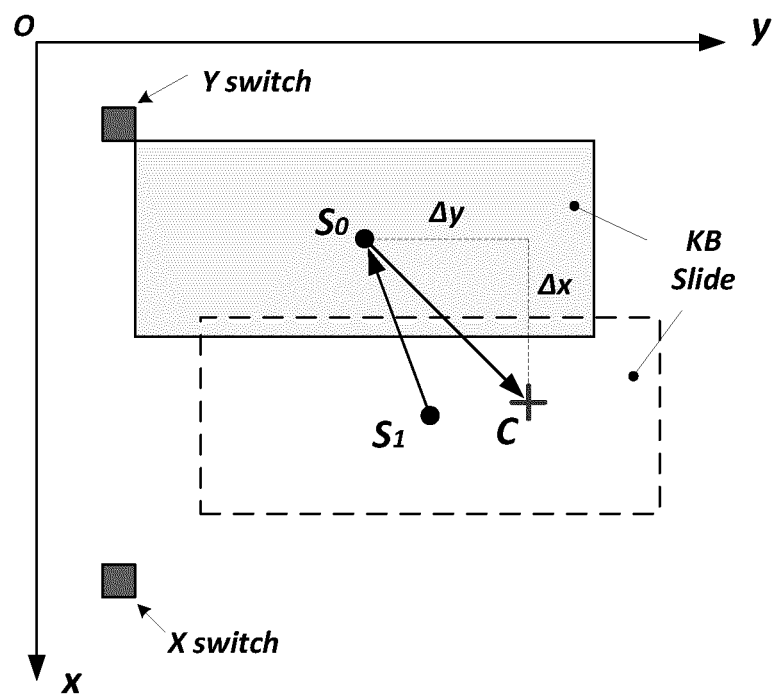
FIG. 5 illustrates a slide "centering" procedure.

The above described system can be used to capture images from slides from which the RBCs are counted. The slides are typically prepared according to the standard clinical method of quantifying fetal-maternal hemorrhage—the Kleihauer-Betke (KB) test. Due to unevenness of the RBCs located on a KB slide, which is more severe on the far left and far right, images should be captured around the centre of the slide. Hence, slide centering is advantageously performed by the automated system. FIG. 5 shows an exemplary movement sequence to automatically center the KB slide. To achieve automatic slide centering, motion limit switches (X switch and Y switch in FIG. 5) are added to the motorized X-Y microscope stage for detecting the motion limit of the microscope stage. The initial position of the KB slide under the field of view is shown by the dashed rectangle with center at $S_1$ in FIG. 5. The switches on the microscope stage enable the system to automatically shift $S_1$ to $S_0$. With this known position relative to the motion limits of the microscope stage, the system then moves the KB slide to the center of the field of view ('C' in FIG. 5), which is the intersection point between the central axis of the object and the horizontal plane of the X-Y stage. Algorithms for implementing such centering are generally known in the art and are not described in further detail.

Figure 6:
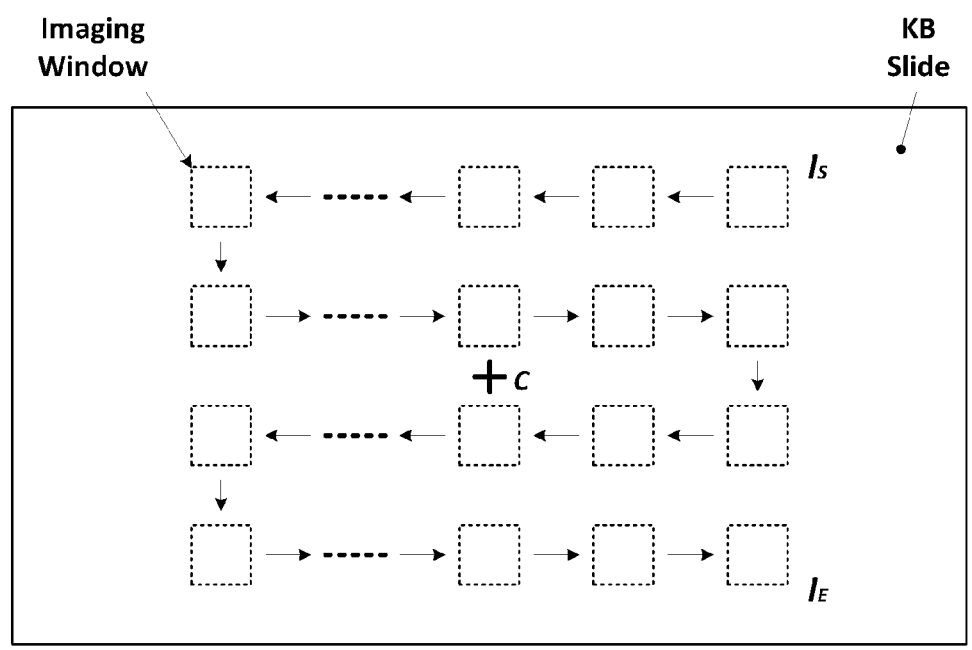
FIG. 6 illustrates the movement pattern of the microscope used to capture RBC images.
Figure 7:
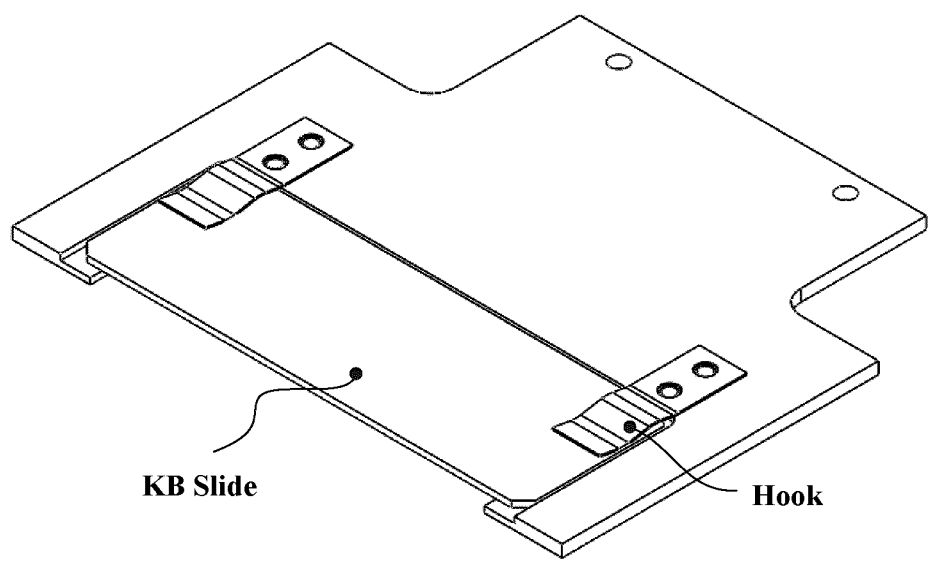
FIG. 7 is an exemplary clamping mechanism for keeping a KB slide in place during X-Y stage motion.

FIG. 6 shows a sample movement sequence for capturing cell images in order to minimize changes in direction. After slide centering, the system moves the X-Y microscope stage with predetermined distances in both X and Y directions and make the first image frame to capture ($I_S$ in FIG. 6) present under the field of view. The system captures the first image $I_S$ and last image $I_E$, according to the moving sequence labeled in FIG. 6. This moving sequence can lessen the impact of dead zones or missing steps which occur inherently when a stepper motor changes rotation directions. To keep the sample within focus during multi-image capturing, the KB slide is clamped tightly on the X-Y microscope stage with two hooks, as illustrated in FIG. 7. Since two fields of view correspond to a small physical distance, obtaining a few hundred images from different regions of a KB slide does not require large travels of the X-Y microscope stage; hence, focal plane changes are not significant. However, clamping the KB slide down is proven necessary to keep all images in focus throughout the scanning/image capturing process. The clamp design avoids Z-focus adjustment and simplifies the hardware and control complexity.

B. Image Processing

Figure 8:
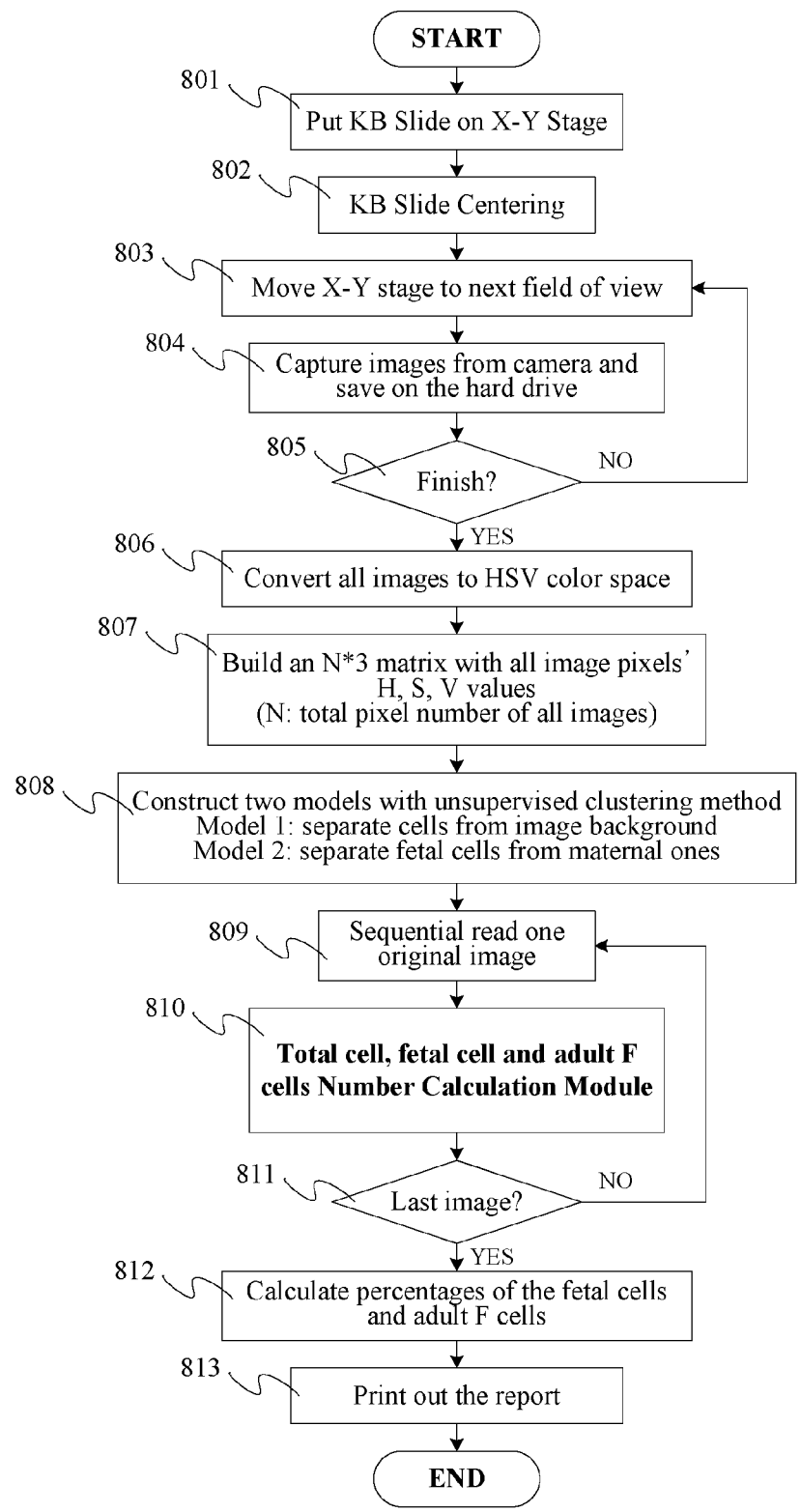
FIG. 8 is a flowchart showing one embodiment of the present invention.

FIG. 8 shows an exemplary method according to the invention, which incorporates the system described above and the novel image processing techniques according to the invention. In step 801, a slide prepared for KB testing is placed on the X-Y microscope stage and clamped tightly by a specimen holder. At step 802, automatic centring is completed. In step 803 and 804, sequential images are captured, according to the sequence of motion as illustrated in FIG. 6, through a color camera connected to the microscope and saved on a computer hard drive, network storage space, or other computer readable medium. Once an image is captured and saved, the motorized stage is controlled by the system to move to the next window/field of view for capturing the next image, and this process repeats until the camera scans over the slide and sufficient images are captured (i.e., until $I_E$ in FIG. 6). One skilled in the art will appreciate that other approaches are also contemplated, provided that a sufficient number of images can be obtained.

Cell images are taken in color, and would have been counted manually in the prior art. Such manual counting requires the subjective assessment of a technologist or other user to identify and classify each of the cells under a microscope. The methods described in the current invention, in addition to providing an automated approach, also provides for a quantitative assessment for identifying and classifying fetal RBCs, maternal RBCs, and adult F RBCs. This quantitative assessment results in greater consistency between slides and a more uniform approach to identifying fetal RBCs. Furthermore, prior art subjective approaches have difficulty in distinguishing between adult F RBCs (i.e., adult RBCs with fetal haemoglobin present in adults) and fetal RBCs themselves. The present invention aims to not only distinguish maternal RBCs from fetal RBCs, but to also detect adult F RBCs.

Typically, there are approximately 500 cells in each image under a 20× microscope. In order to obtain counting results with high accuracy, a large number of cells are counted. Accordingly, step 805 checks for a suitable number of images, in a working example, this would be 120 images captured from different areas around the KB slide centre so that, preferably, approximately 60,000 RBCs are counted.

Variations in cell color and the extent of cell overlapping exist across different KB slides. Hence, an unsupervised clustering method can be suitable to use for RBC count. In step 806, the 120 original images are converted to the hue-saturation-value (HSV) color space. The HSV color space is a known representation for representing images in RGB colors and is not described in further detail, however, the application to the field of the current invention is novel.

Figure 9:
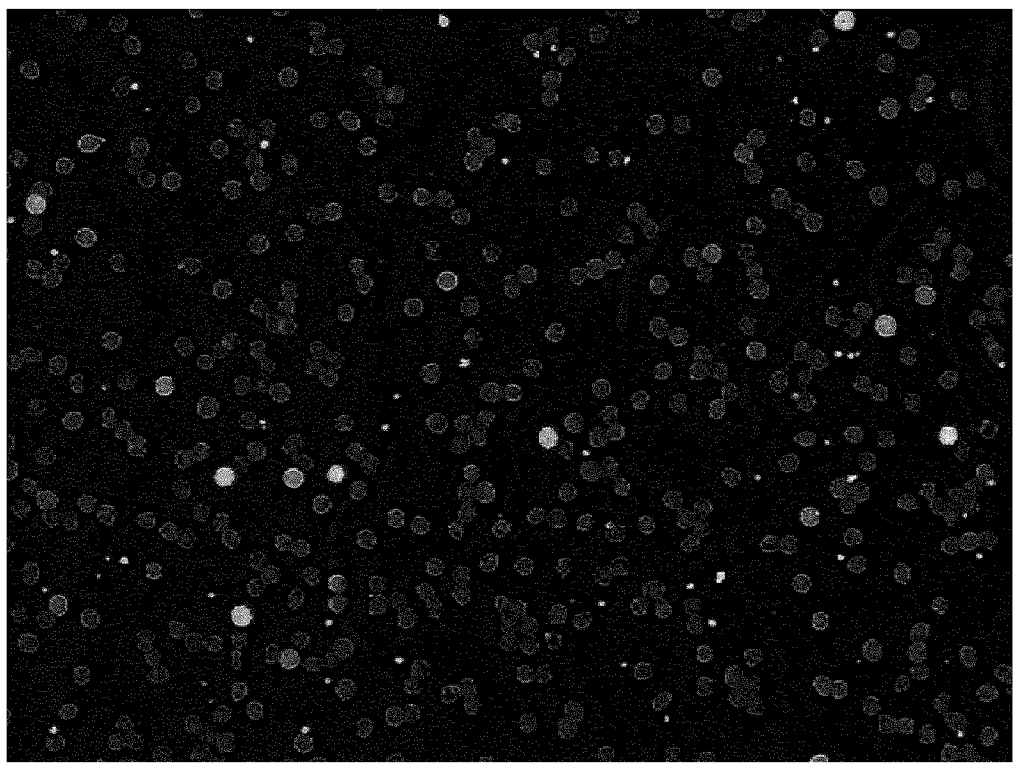
FIG. 9 shows an example cell image in the saturation channel.

In step 807, an N×3 dimensional matrix $M_{HSV}$ constructed with all image pixels' H, S, and V values is fit as an input with an unsupervised clustering algorithm (e.g., Gaussian mixture distribution), where N is the total pixel number of all images captures. For example, when the image resolution is 800 pixel×600 pixel and 120 images are processed, N equals to 800×600×120. In step 808, a pair of models are generated. Model 1 is generated for separating RBCs from the image background after fitting a Gaussian mixture distribution on $M_{HSV}$. In the converted color space of Model 1, fetal and maternal RBCs show different values in the saturation channel of the HSV space (the saturation channel image is shown in FIG. 9). Next, a matrix is generated by combining the cells' saturation values into an $N_{Scell} \times 3$ matrix $M_{Scell}$. Model 2 is generated by fitting a Gaussian mixture distribution to $M_{Scell}$. With Model 2, fetal RBCs can be separated from maternal ones. In step 809 and 810, after the generation of Model 1 and Model 2, captured images are processed sequentially to count numbers of total RBCs, adult F RBCs and fetal RBCs through a Number Calculation Module.

In step 811, if all saved images have been processed, the total numbers of RBCs, fetal RBCs, adult F RBCs and their concentrations are calculated in step 812. In step 813, test result is reported.

Figure 10:
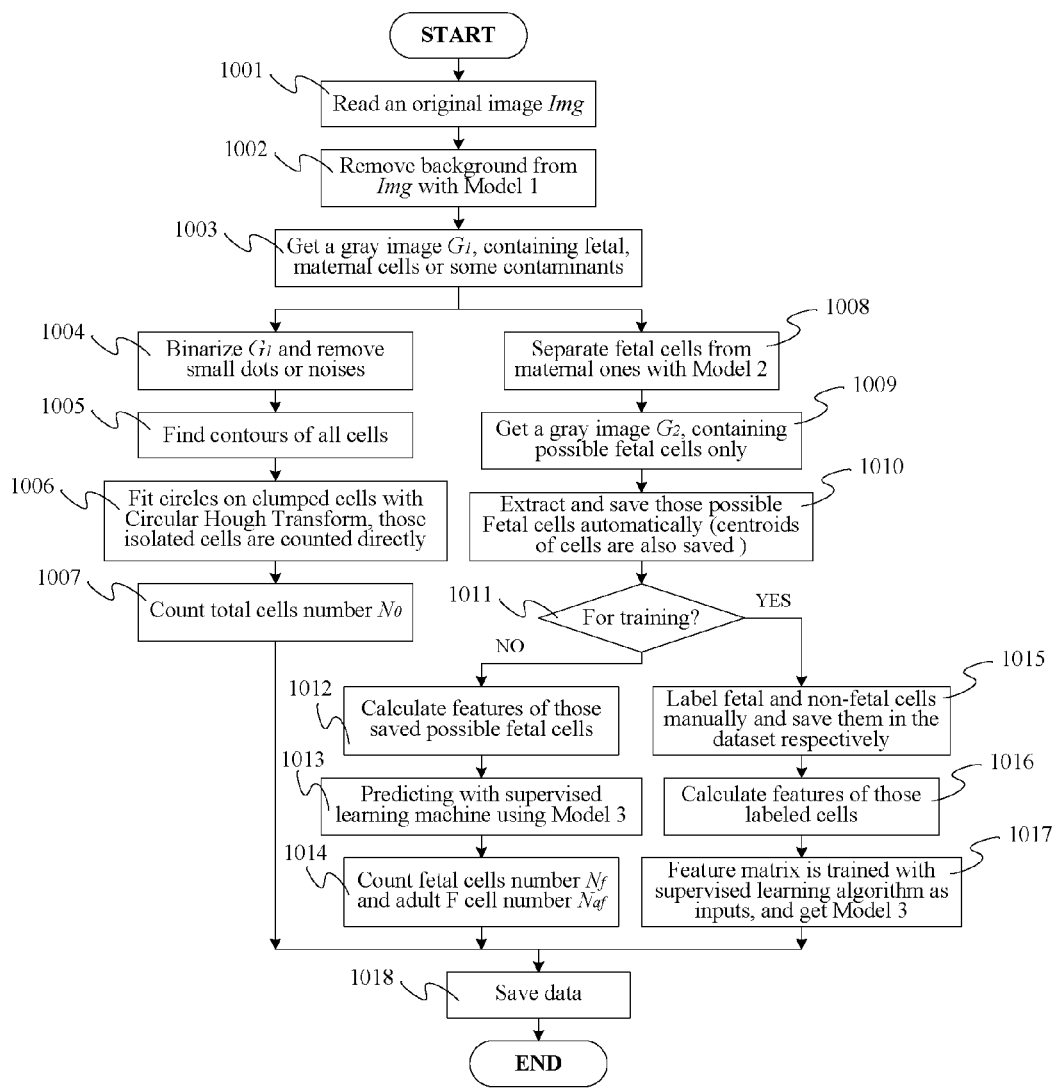
FIG. 10 is a flowchart showing details of another embodiment of the invention where total RBCs, fetal RBCs, and adult F RBCs are counted.
Figure 11:
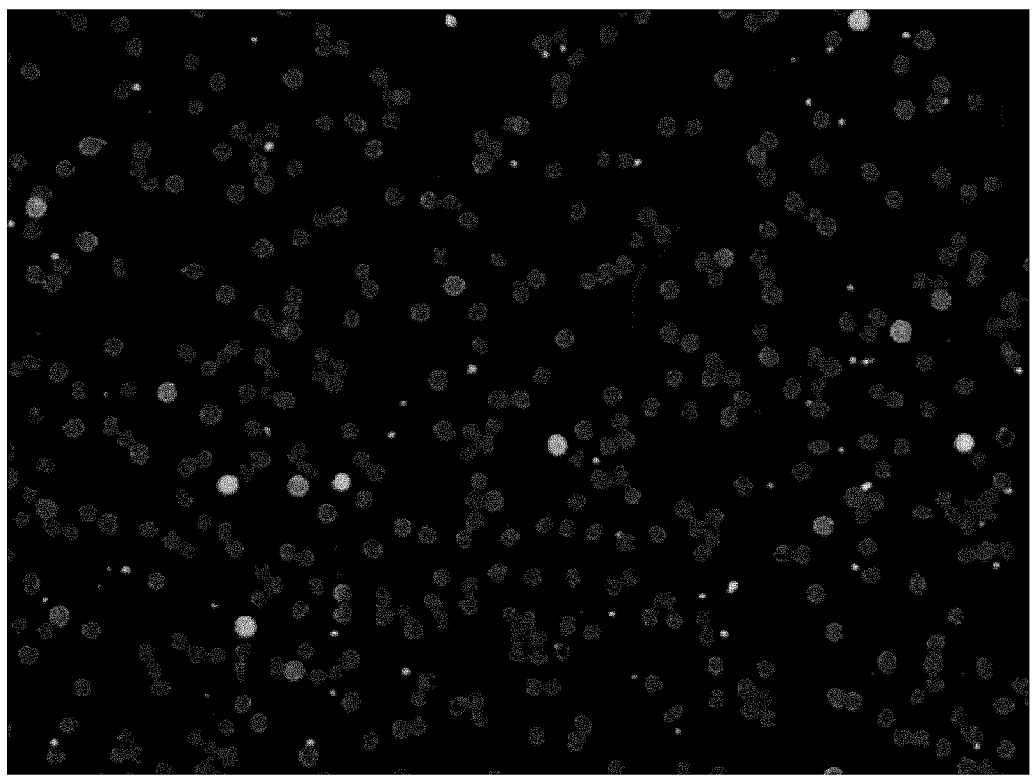
FIG. 11 illustrates a Model 1 gray image (G1) without background information.

The Number Calculation Module for determining the number of maternal and fetal RBCs is shown in the flowchart of FIG. 10. The Number Calculation Module is typically implemented by way of computer readable instructions on a computer readable medium that when executed by a computer system including a processor results in the method steps being executed. In step 1001 and 1002, an original image (denoted by Img) is read into the memory and its background image data are removed with Model 1. In step 1003, a gray image $G_1$ containing only fetal, maternal RBCs, and contaminants is obtained and illustrated in FIG. 11. Contaminants are those features or image portions that are not readily identifiable as background data and had not been removed in the previous step. Contaminants may also include adult F RBCs, which have some characteristics similar to fetal RBCs. There are two main steps for processing the images: one is counting all RBCs, and the other is counting fetal RBCs and adult F RBCs (i.e., distinguishing fetal from adult F RBCs). In step 1004, the gray-scale image $G_1$ is binarized with a threshold value of zero. Those pixel intensities that are higher than zero will be set to 1 in the binary image.

Figure 12:
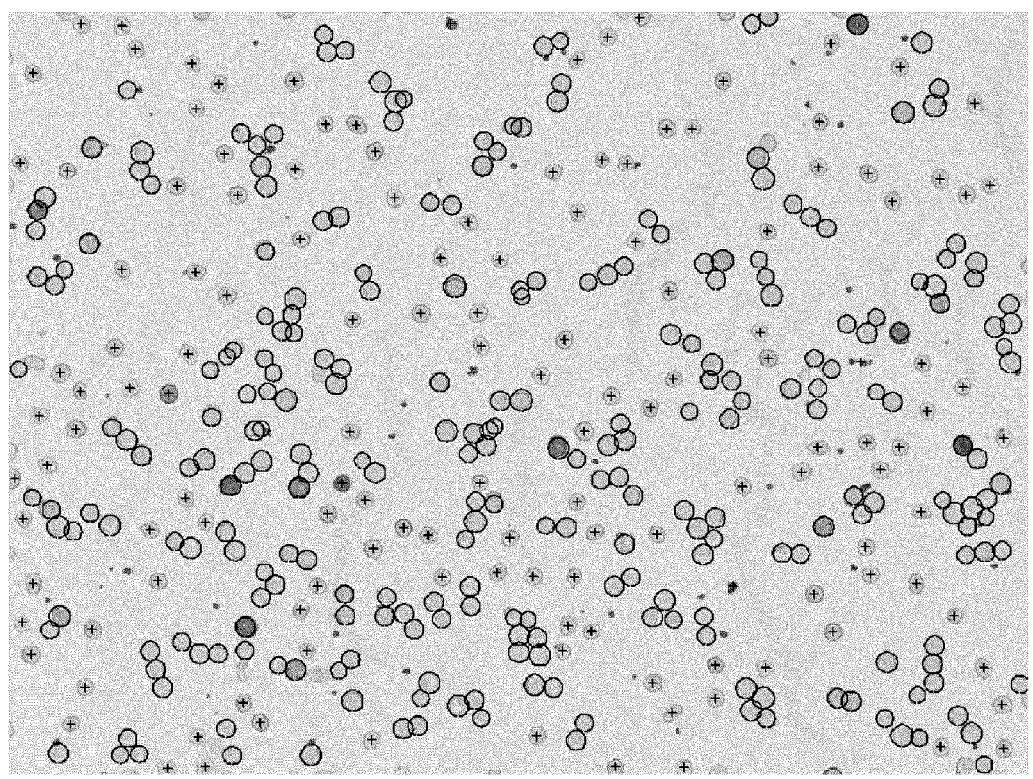
FIG. 12 illustrates the overlapping cells with circles and isolated cells with plus labels.

Overlapped/connected RBCs are contained in the binarized image. The circular Hough transform (CHT) algorithm may be used to recognize and segment the overlapping RBCs by fitting circles on cell contours. In step 1005, all cell contours can be detected with operators such as Canny and LoG within the binarized image. In step 1006, the detected edge points of RBCs and the assumed range of RBC radius allow the potential RBC targets to be circled out. The radius of an RBC is approximately 20 pixels on average under a 20× microscope objective. Therefore, the radii range for circle detection can be assumed in the interval of [20×0.8, 20×1.5] for instance. Cells with a radius out of this range will be ignored during calculation. Therefore, those contaminants with irregular shapes are not counted due to their large radii and different colors. Experimental results have proven that overlapped/connected cells can be recognized effectively. The processed image with labelled circles (detected overlapping cells) and isolated cells with plus signs is shown in FIG. 12. In step 1007, the number of fitted circles and black plus signs is taken as the total number of the RBCs in the image.

The next step is to count the number of fetal RBCs and the number of adult F RBCs, and calculate respective percentages. In captured color images, fetal RBCs appear deep red, bright and smooth inside while maternal RBCs appear light and pinkish. Therefore, color information is the first cue used in this invention to distinguish fetal cells from maternal ones. Unfortunately, due to the cell color, size or overlapping variations across different KB slides, relying solely on saturation channel information-based thresholding is not a reliable method. The fetal RBC percentage may be overestimated or underestimated. Hence, besides color information, other features including cell size, roundness, gradient, saturation difference between a cell and the whole slide are used to distinguish fetal RBCs from maternal ones in this invention. Based on these features, classifiers (e.g., neural network, support vector machines, k-nearest neighbours, Gaussian mixture model, naive Bayes, decision tree or RBF classifiers) can be used to classify cells into fetal RBCs, maternal RBCs and adult F RBCs. These classifiers can be trained via a supervised learning algorithm to improve the classification accuracy. Therefore, datasets for training are preferably constructed.

In step 1008 and 1009, a gray-scale image $G_2$ (see FIG. 13) is achieved after separating fetal RBCs from maternal ones as per Model 2. In step 1010, possible fetal cells within image $G_2$ are then extracted and corresponding color cells are saved. Extracted cell centroid coordinates with their corresponding original image names are also saved for future validation or assessment by hospital staff. In step 1011, if extracted cells are for training the software system, they will be labelled "positive" or "negative" manually and saved in respective folders in step 1015. For accuracy and reliability, a high number of manually labelled "positive" or "negative" cells from a high number of KB slides should be used to construct the feature vector in step 1016. In step 1017, a classification model (Model 3) is built after fitting the feature vector with a classifier like K-nearest neighbours (KNN).

Figure 13:
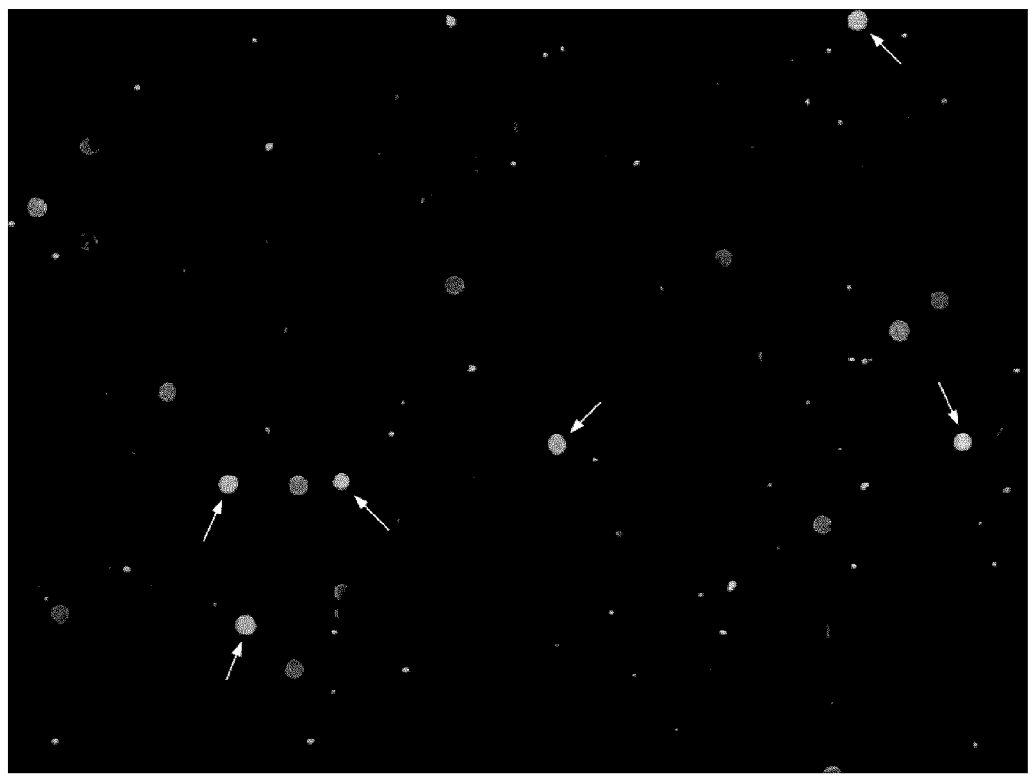
FIG. 13 illustrates a gray color image (G2) containing possible fetal RBCs.

In step 1011, if extracted cells are for cell predicting and counting in KB test, features of those extracted cells are calculated in step 1012, sent to the algorithm as an input, and predicted with Model 3 in step 1013. In step 1014, if $p_i > T_f$, the cell will be considered as a fetal RBC. If $T_{af} < p_i \leq T_f$, it is considered to be an adult F cell. Others will be considered as maternal cells. Here, $p_i$ is the similarity between i-th possible fetal cell and manually labelled "positive" cells. $T_f$ and $T_{af}$ are the respective threshold values for classifying fetal RBCs and adult F RBCs which can be statistically calculated through gating a high number of KB slides. In step 1018, images' total RBC number, total adult F RBC number, total fetal RBC number and other intermediate results will be saved on the harddrive. In FIG. 13, those RBCs indicated with arrows are considered positive fetal cells while others are negative adult RBCs or contaminants.

After all captured images are processed, the total cell number, total adult F cell number and total fetal cell number of the slide (denoted by $N_0$, $N_{af}$, $N_f$ separately) are determined. The percentages of fetal RBCs and adult F cells are subsequently calculated according to $R_f = N_f/N_0$ and $R_{af} = N_{af}/N_0$, respectively.

Finally, as will be appreciated by one skilled in the art, the above described embodiments are exemplary only, with various alternatives and modifications contemplated. For example, the specific algorithms named herein are exemplary only and modifications or alternate algorithms accomplishing the same or analogous results are also contemplated. Furthermore, any means of capturing images from slides are contemplated, as are means of moving slides, obtaining images and processing the images. The scope of the invention is only to be limited by the claims that follow.

The invention claimed is:

1. A system for counting fetal and maternal red blood cells (RBCs) comprising a microscope and image capturing device to capture a plurality of images from a slide holding the fetal and maternal RBCs; wherein said microscope is configured to centre said slide such that said plurality of images are captured by following a predetermined path around the centre of said slide; a non-transitory computer readable medium for storing said plurality of images; a processor for executing computer readable instructions stored on a non-transitory computer readable medium; wherein said computer executable instructions include instructions for: converting said images into hue-saturation-value (HSV) color space and creating an N*3 matrix storing the H, S and V values for each pixel of said images; identifying RBCs from said plurality of images; distinguishing between fetal and maternal RBCs; and counting said fetal and maternal RBCs.

2. The system according to claim 1, wherein said microscope includes an X-axis linear motion system and a Y-axis linear motion system.

3. The system according to claim 2, wherein said microscope is in communication with a controller including a driver for each of said X and Y axis linear motion systems.

4. The system according to claim 3, wherein said X-axis linear motion system and said Y-axis linear motion system are independently controllable.

5. The system according to claim 1, wherein said predetermined path consists of an S-shaped path.

6. The system according to claim 5, wherein said plurality of images comprises approximately 120 images.

7. The system according to claim 1, wherein said computer executable instructions further include instructions for generating a first model (Model 1) and a second model (Model 2); wherein Model 1 is used to distinguish red blood cells from the image background and Model 2 is used to separate fetal red blood cells from maternal red blood cells.

8. The system according to claim 7, wherein Model 1 is generated by computer executable instructions for: detecting contours on each said images; and circle fitting said contours using predetermined criteria for defining possible cells.

9. The system according to claim 8, wherein said instructions further include an algorithm for identifying overlapping cells.

10. The system according to claim 8, wherein said algorithm is a circular Hough transform algorithm.

11. The system according to claim 7, wherein Model 2 is generated by computer executable instructions for: converting each image to a gray image; and distinguishing potential fetal red blood cells from maternal red blood cells.

12. The system according to claim 11, wherein said computer executable instructions further include instructions for: generating a second gray image containing said potential fetal red blood cells; distinguishing between fetal red blood cells and adult F red blood cells.

13. The system according to claim 11, wherein said distinguishing of potential fetal red blood cells from maternal red blood cells includes an algorithm including feature vectors including at least one feature from the group consisting of cell size, roundness, gradient, saturation difference and a combination of same; and further wherein feature values for each of fetal red blood cells and maternal red blood cells are stored on said non-transitory computer readable medium.

14. The system according to claim 12, wherein said distinguishing of fetal red blood cells from adult F red blood cells includes an algorithm including feature vectors including at least one feature from the group consisting of cell size, roundness, gradient, saturation difference and a combination of same; and further wherein feature values for each of fetal red blood cells and adult F red blood cells are stored on said non-transitory computer readable medium.

15. The system according to claim 11, wherein said distinguishing is conducted using a supervised learning model selected from the group consisting of K-nearest neighbors, Gaussian mixtures, decision trees and other.

16. A computer executable method for counting fetal and maternal red blood cells (RBCs) comprising: obtaining by a camera mounted on a microscope a plurality of images from a slide by centering said slide and capturing said plurality of images by following a predetermined path around the centre of said slide; converting said images into hue-saturation-value (HSV) color space and creating an N*3 matrix storing the H, S and V values for each pixel of said images; identifying by a computer processor red blood cells from said plurality of images; distinguishing by the computer processor between fetal and maternal red blood cells; and counting by the computer processor at least said fetal red blood cells.

17. The method according to claim 16, wherein said predetermined path consists of an S-shaped path.

18. The method according to claim 17, wherein said plurality of images comprises approximately 120 images.

19. The method according to claim 16, further comprising generating a first model (Model 1) and a second model (Model 2); wherein Model 1 is used to distinguish red blood cells from the image background and Model 2 is used to separate fetal red blood cells from maternal red blood cells.

20. The method according to claim 19, wherein Model 1 is generated by: detecting contours on each said images; and circle fitting said contours using predetermined criteria for defining possible cells.

21. The method according to claim 19, wherein Model 2 is generated by: converting each image to a gray image; and distinguishing potential fetal red blood cells from maternal red blood cells.

22. The method according to claim 19, further comprising generating a second gray image containing said potential fetal red blood cells; distinguishing between fetal red blood cells and adult F blood cells.

23. The method according to claim 19, wherein said distinguishing of potential fetal red blood cells from maternal red blood cells includes executing an algorithm including feature vectors including at least one feature from the group consisting of cell size, roundness, gradient, saturation difference and a combination of same; and further wherein feature values for each of fetal red blood cells and maternal red blood cells are stored on a non-transitory computer readable medium.

24. The method according to claim 19, wherein said distinguishing of fetal red blood cells from adult F red blood cells includes executing an algorithm including feature vectors including at least one feature from the group consisting of cell size, roundness, gradient, saturation difference and a combination of same; and further wherein feature values for each of fetal red blood cells and adult F red blood cells are stored on said non-transitory computer readable medium.

25. The method according to claim 19, wherein said distinguishing is carried our using a supervised learning model selected from the group consisting of K-nearest neighbors, Gaussian mixtures, decision trees and other.

26. A system for counting fetal and maternal red blood cells (RBCs) comprising a microscope and image capturing device to capture a plurality of images from a slide holding the fetal and maternal RBCs; wherein said microscope is configured to centre said slide such that said plurality of images are captured by following a predetermined path around the centre of said slide, said predetermined path consisting of an S-shaped path; a non-transitory computer readable medium for storing said plurality of images; a processor for executing computer readable instructions stored on a non-transitory computer readable medium; wherein said computer executable instructions include instructions for: identifying RBCs from said plurality of images; distinguishing between fetal and maternal RBCs; and counting said fetal and maternal RBCs.

27. A computer executable method for counting fetal and maternal red blood cells (RBCs) comprising: obtaining by a camera mounted on a microscope a plurality of images from a slide by centering said slide and capturing said plurality of images by following a predetermined path around the centre of said slide, said predetermined path consisting of an S-shaped path; identifying by a computer processor red blood cells from said plurality of images; distinguishing by the computer processor between fetal and maternal red blood cells; and counting by the computer processor at least said fetal red blood cells.

* * * * *